United States Patent
Edwards et al.

(10) Patent No.: US 11,715,570 B1
(45) Date of Patent: Aug. 1, 2023

(54) SYSTEMS AND METHODS TO CONNECT CARE SEEKERS WITH CARE PROVIDERS FOR CARETAKING NEEDS

(71) Applicant: Helpr, Inc., Santa Monica, CA (US)

(72) Inventors: Kasey Mackensie Edwards, Santa Monica, CA (US); Rebecca Meghan Klauber, Santa Monica, CA (US)

(73) Assignee: Helpr, Inc., Rancho Palos Verdes, CA (US)

( * ) Notice: Subject to any disclaimer, the term of this patent is extended or adjusted under 35 U.S.C. 154(b) by 598 days.

(21) Appl. No.: 16/583,745

(22) Filed: Sep. 26, 2019

(51) Int. Cl.
*G06Q 10/10* (2023.01)
*G16H 80/00* (2018.01)
*G06F 16/903* (2019.01)
*G06F 16/907* (2019.01)
*G06F 3/0482* (2013.01)

(52) U.S. Cl.
CPC .......... *G16H 80/00* (2018.01); *G06F 3/0482* (2013.01); *G06F 16/903* (2019.01); *G06F 16/907* (2019.01)

(58) Field of Classification Search
CPC ...... G16H 80/00; G06F 16/907; G06F 16/903; G06F 3/0482; G06Q 10/1053
See application file for complete search history.

(56) References Cited

U.S. PATENT DOCUMENTS

| | | | |
|---|---|---|---|
| 2014/0330608 A1* | 11/2014 | Arthur | F16H 61/0028 705/7.19 |
| 2015/0199744 A1* | 7/2015 | Tolvanen et al. | G06F 16/9537 707/737 |
| 2015/0248649 A1* | 9/2015 | Avats | G06Q 10/1053 705/321 |
| 2016/0092695 A1* | 3/2016 | Novotny et al. | G06F 16/955 726/28 |
| 2019/0080309 A1* | 3/2019 | Goodwin et al. | G06Q 20/401 |

* cited by examiner

*Primary Examiner* — Haoshian Shih
(74) *Attorney, Agent, or Firm* — Esplin & Associates, PC

(57) ABSTRACT

Systems and methods to connect care seekers with care providers for caretaking needs are disclosed. Exemplary implementations may: store seeker profiles for care seekers and/or provider profiles for care providers; present a user interface configured to facilitate generation of individual provider profiles; receive care seeker-defined characteristics of potential care providers; generate new individual provider profiles for individual potential care providers; and/or perform other operations.

20 Claims, 5 Drawing Sheets

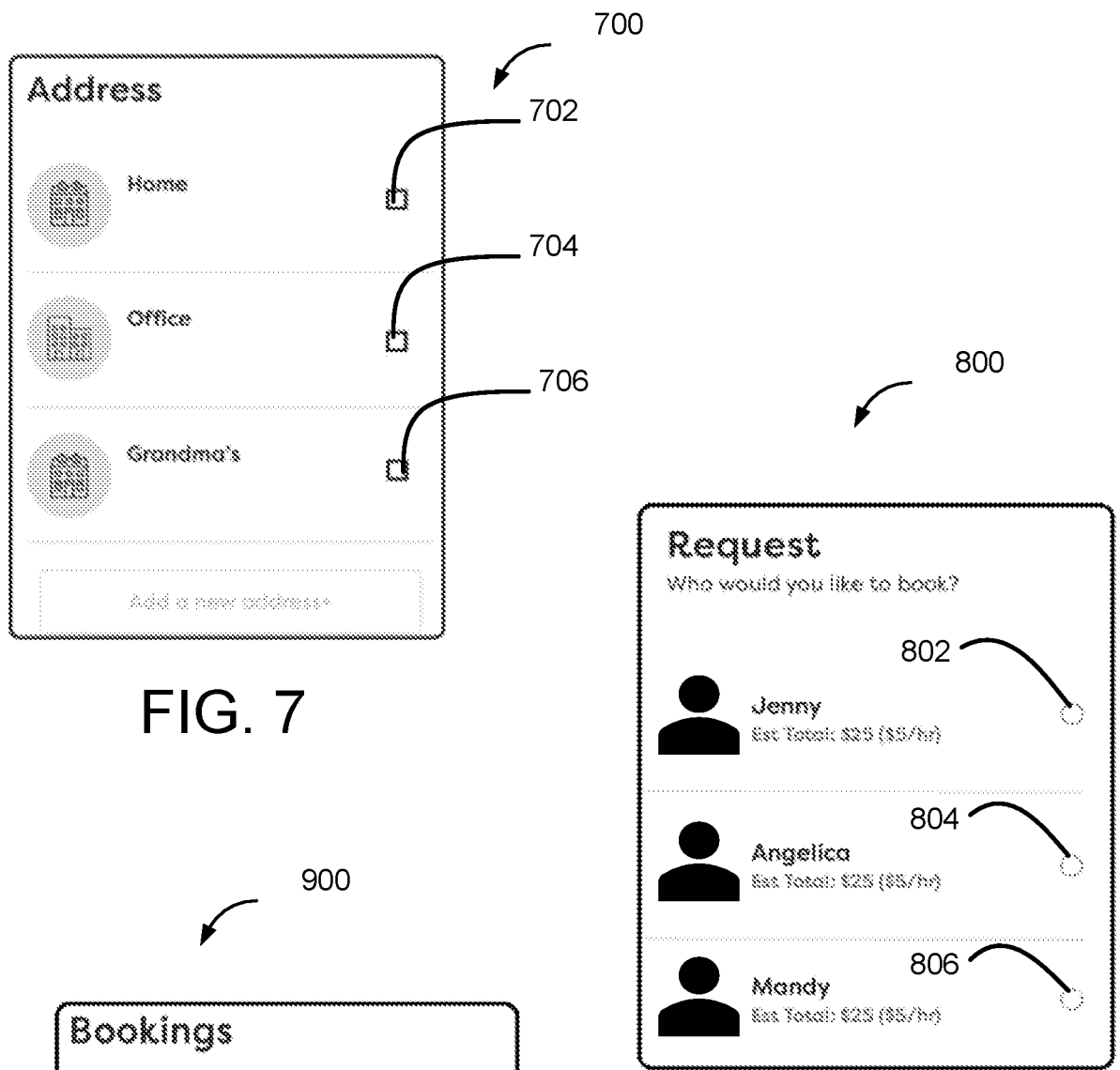
FIG. 7
FIG. 8
FIG. 9

SYSTEMS AND METHODS TO CONNECT CARE SEEKERS WITH CARE PROVIDERS FOR CARETAKING NEEDS

FIELD OF THE DISCLOSURE

The present disclosure relates to systems and methods to connect care seekers with care providers for caretaking needs.

BACKGROUND

Some healthcare providers and/or employers may subsidize costs for the caretaking of children. Professional caregivers (herein also referred to as "care providers") may work within the context of a center-based care (e.g., such as daycare for children, nursing homes for elderly, etc.) or a home-based care (e.g., nannies or family care, at-home elderly care, etc.). Childcare providers may also be required to have certification in first aid and/or CPR. Often background checks, drug testing, and reference verification are performed. Adults and/or elders may also be subjects of caretaking needs in the case of short-term medical recovery and/or ongoing care needs.

SUMMARY

When an individual seeks a care provider to satisfy caretaking needs, they often encounter many challenges. For example, a care seeker will typically have to sift through many potential care providers based on experience, age, availability, and face to face interviews, among other qualities. When subsidized by healthcare, the quantity and/or quality of in-network care providers may be limited. These challenges are often compounded in cases of last-minute caretaking needs. Typically, a care seeker may end up calling upon grandparents, in-laws, friends, friends-of-friends, and/or babysitters to satisfy their caretaking needs. Repeatedly using friends and family as care providers may result in some unspoken resentment towards the care seekers, as such caretaking is often provided out of love and free of charge.

One aspect of the present disclosure relates to a system configured to connect care seekers with care providers for caretaking needs. One or more implementations of the system may address challenges existing in conventional solutions for care seekers seeking care providers. In particular, the system may include a user-generated network of care providers which may be accessed, searched, and used to book caretaking appointments. The system may be integrated with healthcare systems and/or private providers of healthcare in order to facilitate direct payment to care providers. Users who are care seekers may request that friends and/or family become approved as care providers within the system. The friends and/or family may become users of the system who are care providers and may utilize the system to receive payment in exchange for caretaking services. Accordingly, users who are care seekers may develop a network of care providers which they know and trust and which can be easily accessed, booked, and paid through the features and/or functionally of the system.

One or more implementations of a system to connect care seekers with care providers for caretaking needs may include one or more of non-transitory electronic storage, one or more hardware processors configured by machine-readable instructions, and/or other components.

The non-transitory electronic storage may be configured to store one or more of seeker profiles, provider profiles, and/or other information. Seeker profiles may comprise profiles for users who may be care seekers. Individual seeker profiles may define values of seeker parameters. The values of the seeker parameters may describe characteristics of the care seekers. By way of non-limiting illustration, the seeker profiles may comprise a first seeker profile for a first user who is a care seeker.

Provider profiles may comprise profiles for users of the system who may be care providers. Individual provider profiles may define values of provider parameters. The values of the provider parameters may describe characteristics of the care providers. By way of non-limiting illustration, the provider profiles may comprise a first provider profile for a second user who is a care provider.

The processor(s) may be configured to effectuate presentation of a user interface on computing platforms of users. The user interface may be configured to facilitate generation of the individual provider profiles by individual care seekers and/or individual care providers. By way of non-limiting illustration, the user interface may be presented on a first computing platform of the first user who may be a care seeker.

The processor(s) may be configured to receive, via the user interface, user entry and/or selection of individual sets of characteristics of individual potential care providers. By way of non-limiting illustration, user entry and/or selection of a first set of characteristics of a first potential care provider may be received from the first user via the user interface.

The processor(s) may be configured to generate new provider profiles for the potential care providers. The potential care providers may then, as such, be defined as users within the system who are care providers. By way of non-limiting illustration, a second provider profile may be generated for the first potential care provider such that the first potential care provider may comprise a third user who is a care provider.

As used herein, any association (or relation, or reflection, or indication, or correspondence) involving servers, processors, client computing platforms, and/or another entity or object that interacts with any part of the system and/or plays a part in the operation of the system, may be a one-to-one association, a one-to-many association, a many-to-one association, and/or a many-to-many association or N-to-M association (note that N and M may be different numbers greater than 1).

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 7 illustrates an exemplary user interface, in accordance with one or more implementations.

FIG. 8 illustrates an exemplary user interface, in accordance with one or more implementations.

FIG. 9 illustrates an exemplary user interface, in accordance with one or more implementations.

DETAILED DESCRIPTION

Figure 1:
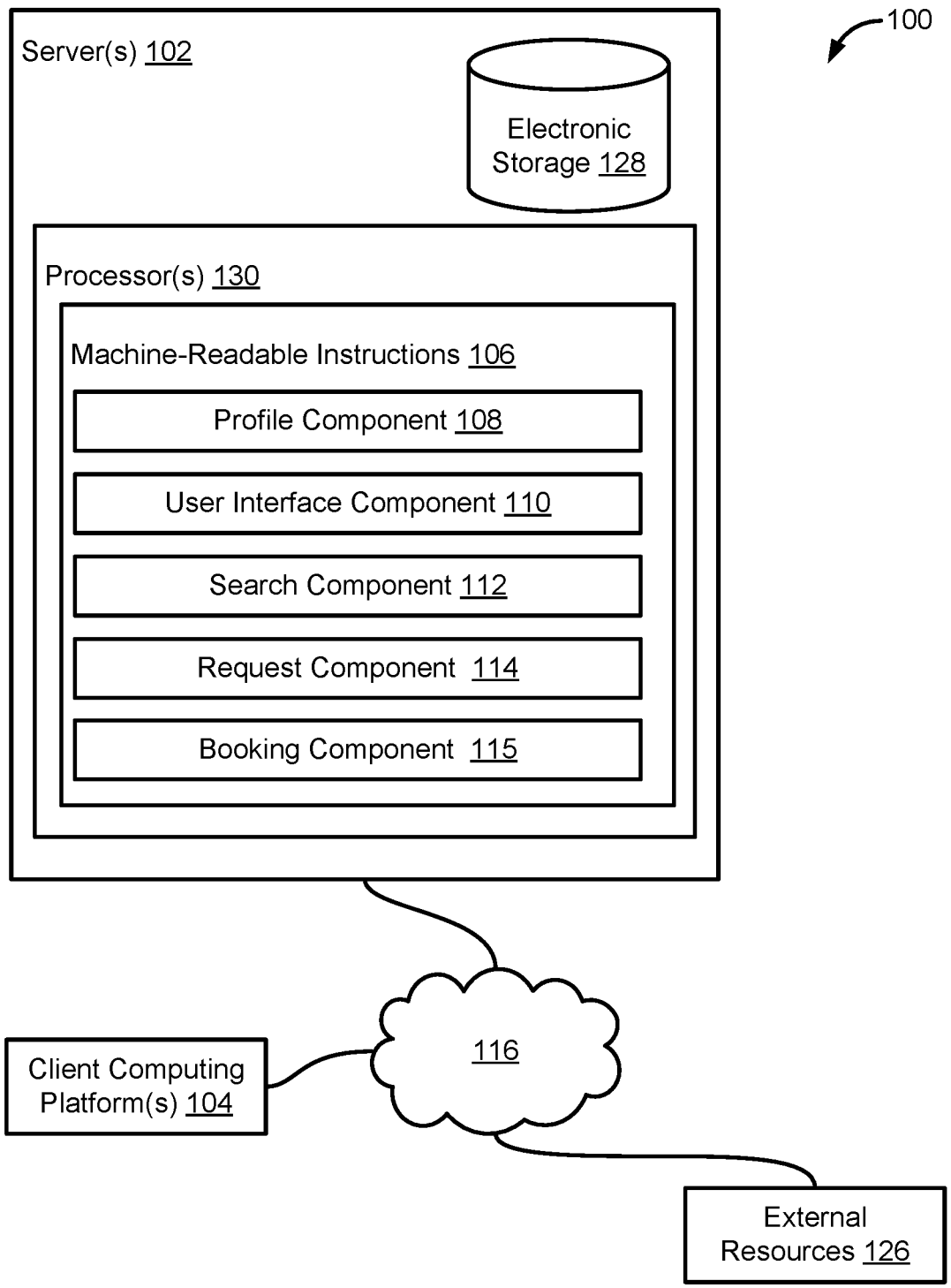
FIG. 1 illustrates a system configured to connect care seekers with care providers for caretaking needs, in accordance with one or more implementations.

FIG. 1 illustrates a system 100 configured to connect care seekers with care providers for caretaking needs, in accordance with one or more implementations. Users of the system 100 who are care seekers may request that friends, family, and/or other individuals become approved as care providers within the system 100. The friends, family, and/or other individuals may become users of the system 100 who are care providers and thus may utilize the system 100 to receive payment in exchange for caretaking services. Accordingly, users who are care seekers may develop a network of care providers which they know and trust and which can be easily accessed, booked, and paid through the features and/or functionally of the system 100.

In some implementations, system 100 may include one or more of one or more servers 102, one or more client computing platforms 104, external resources 126, and/or other components. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may include one or more of non-transitory electronic storage 128, one or more processors 130 configured by machine-readable instructions 106, and/or other components.

The non-transitory electronic storage 128 may be configured to store one or more of seeker profiles, provider profiles, and/or other information.

Seeker profiles may comprise profiles for users who may be care seekers. Individual seeker profiles may define values of seeker parameters. Individual seeker profiles may include videos and/or images of one or more of the care seekers, subjects of caretaking, locations of caretaking (e.g., view of house, location of lockbox, etc.) and/or other content. The values of the seeker parameters may describe characteristics of the care seekers. By way of non-limiting illustration, the seeker profiles may comprise a first seeker profile for a first user who is a care seeker.

The seeker parameters may include one or more of a name parameter, a location parameter, a subject parameter, a status parameter, a payment parameter, and/or other parameters.

A value of a name parameter may define a name characteristic of a user. A name characteristics may include one or more of a legal name, a preferred name, a username, an email address, and/or other information.

A value of a location parameter may define a location characteristic of caretaking. A location characteristic may include one or more of addresses where caretaking is desired, restrictions and/or notes about locations, and/or other information. By way of non-limiting illustration, addresses may include one or more of a home address, a work address, a zip code, a city, a state, and/or other information. Restrictions and/or notes about locations may include one or more of building type indications (e.g., house, apartment, hotel, motel, office, and/or other information), access information (e.g., key location, lock codes, and/or other information), parking instructions, pet information, and/or other information.

A value of a subject parameter may define subject characteristics of a subject of caretaking needs. Subject characteristics of a subject of caretaking needs may include one or more of name, age, gender identify, allergies, exceptionalities, preferences (e.g., with respect to toys, movies, games, books, cartoons, color, etc.), and/or other information.

A value of a status parameter may define a status characteristics of a user. A status characteristics of a user may comprise a qualitative and/or quantitative description of a user as a user within system 100. A status characteristic may include one or more of quantity of upvotes and/or downvotes by other users in the system 100, a rating, a review, a comment, an indication that a background check has been performed, and/or other information.

A value of a payment parameter may define a payment characteristic of a user from which funds are to be paid from. A payment characteristic may include one or more of healthcare provider information, employer information, personal payment information, and/or other information. The healthcare provider information may include one or more of healthcare provider name, account number, and/or other information. The employer information may include employer name, employer contact information, and/or other information. The personal payment information may include personal banking information, credit card information, debit card information, and/or other information.

Provider profiles may comprise profiles for users of the system who may be care providers. Individual provider profiles may define values of provider parameters. Individual provider profiles may include videos and/or images of one or more of the care provider themselves, a mock interview, and/or other content. The values of the provider parameters may describe characteristics of the care providers. By way of non-limiting illustration, the provider profiles may include a first provider profile of a second user who is a care provider.

The provider parameters may include one or more of the name parameter, a location parameter, an age parameter, an experience parameter, a languages parameter, a certification parameter, an education parameter, a cost parameter, a specialties parameter, a relationship parameter, a status parameter, a payment parameter, and/or other parameters.

A value of the name parameter may define a name characteristic of a user. A name characteristics may include one or more of a legal name, a preferred name, a username, an email address, and/or other information.

A value of a location parameter may define a location characteristic of a user. A location characteristic may include one or more of a home address, a work address, a zip code of residence, a city of residence, a state of residence, a location limitation to provide caretaking services (e.g., a geofence), and/or other information.

A value of an age parameter may define an age characteristic of a user. An age characteristics may include one or more of age, birthdate, astrological sign, and/or other information.

A value of an experience parameter may define an experience characteristic of a user. An experience characteristic may include a measure of caretaking experience and/or other information. The measure may be expressed in terms of time (e.g., months, years, decades, etc.), quantity of subjects previously under their supervision, and/or other information.

A value of a languages parameter may define a language characteristic of a user. A language characteristic of a user may include identification of one or more languages in which the user is fluent in, a level of fluency, and/or other information.

A value of a certification parameter may define a certification characteristic of a user. A certification characteristic of a user may include identifications of one or more certifications obtained by the user. A certification may include one or more of CPR, first aid, drug administration, and/or other certifications.

A value of an education parameter may define an education characteristic of a user. An education characteristic may include one or more of schools attended, degrees obtained, calendar year(s) of graduation, and/or other information.

A value of a cost parameter may define a cost characteristic of a user. A cost characteristic of a user may include one or more of a price per unit time for caretaking services, a flat rate for caretaking services, and/or other information.

A value of a specialties parameter may define a specialties characteristic of a user. A specialties characteristic of a user may include specialties that the user is able to provide during care taking. The specialties may be specified with respect to characteristics of the subjects, characteristics of the amount and/or extent of caretaking, and/or other information. Specialties with respect to characteristics of the subjects may include one or more of subjects of certain age and/or age range (e.g., children, elderly, toddlers, teens, etc.), subjects of certain disability and/or exceptionality, and/or other specialty. Specialties with respect to characteristics of the amount and/or extent of caretaking may include one or more of working late nights, working weekends, fulfilling last minute requests, working overnight, performing certain tasks (e.g., drop-off to school, grocery shopping, and/or other tasks), performing pet caretaking needs, and/or other specialties.

A value of a relationship parameter may define a relationship characteristics of a user. A relationship characteristics may include an indication of a relationship to a particular care seeker. A relationship to a care seeker may include one or more of grandparent, sister, brother, in-law, friend, friend-of-friend, part-time employee (e.g., babysitter), neighbor, and/or other indication.

A value of a payment parameter may define a payment characteristic of a user to which funds are to be paid. A payment characteristic may include personal payment information and/or other information. The personal payment information may include personal banking information, credit card information, debit card information, and/or other information.

Its noted that the above descriptions of provider profiles and/or seeker providers are for illustrative purposes only and are not to be considered limiting. Instead, it is to be understood that the profiles may include other information and/or may define respective users in other ways.

In FIG. 1, machine-readable instructions 106 of one or more processors 130 of server(s) 102 may include one or more instruction components. The instruction components may include computer program components. Executing the machine-readable instructions 106 may cause server(s) 102 to facilitate connecting care seekers with care providers for caretaking needs. The instruction components may include one or more of a profile component 108, a user interface component 110, a search component 112, a request component 114, a booking component 115, and/or other instruction components.

The profile component 108 may be configured to obtain, manage, and/or access seeker profiles and/or provider profiles stored by electronic storage 128. Managing seeker profiles and/or provider profiles may include one or more of generating profiles, changing profiles, updating profiles, and/or other features and/or functionality.

User interface component 110 may be configured to effectuate presentation of individual user interfaces on individual client computing platforms of one or more client computing platforms 104. For example, the individual client computing platforms may access a user interface over network 116. A given user interface may be configured to facilitate connecting care seekers with care providers for caretaking needs. An instance of a user interface may include one or more user interface portions. By way of non-limiting illustration, a user interface may include one or more of an input portion, a display portion, and/or other portions. Individual portions may include one or more user interface elements configured to facilitate user interaction with the user interface. By way of non-limiting illustration, user interface elements may include one or more of text input fields, drop down menus, check boxes, display windows, virtual buttons, and/or other elements configured to facilitate user interaction.

An input portion of a user interface may be configured to obtain user input. User input may include one or more of information to generate a provider profile and/or seeker profile, user-provided search queries, user entry and/or selection individual sets of characteristics of individual potential care providers, and/or other input. In some implementations, the use of the term "potential" may refer to an individual who has yet to establish a profile within the system 100.

In some implementation, user interface may be configured to obtain user entry and/or selection by the individual potential care seekers of individual sets of characteristics of the individual potential care seekers to generate new seeker profiles. By way of non-limiting illustration, individual user interface elements may correspond to individual seeker parameters. User input into the individual user interface elements may define the corresponding values of the individual seeker parameters.

In some implementations, the user interface may be configured to obtain user entry and/or selection by the individual potential care providers of individual sets of characteristics of the individual potential care providers to generate new provider profiles. By way of non-limiting illustration, individual user interface elements may correspond to individual provider parameters. User input into the individual user interface elements may define the corresponding values of the individual provider parameters.

In some implementation, user interface may be configured to obtain user entry and/or selection by the individual care seekers of individual sets of characteristics of individual potential care providers to generate new provider profiles. By way of non-limiting illustration, individual user interface elements may correspond to individual provider parameters. User input into the individual user interface elements may define the corresponding values of the individual provider parameters. By way of non-limiting illustration, user entry and/or selection of a first set of characteristics of a first potential care provider may be received from the first user via the user interface.

In some implementation, user interface may be configured to obtain user entry and/or selection of search queries. A user-provided search query may include a query to search through the provider profiles to find one or more care providers to engage their services. In some implementations, a user-provided search query may specify one or more of subject information, timing information, location information, and/or other information.

The subject information may identify and/or describe one or more subjects having caretaking needs. The subject information may include one or more of the values of the subject parameters selected from the seeker profiles. By way of non-limiting illustration, individual user interface elements may correspond to individual subjects. User input into the individual user interface elements (e.g., selection of a checkbox) may incorporate the information about the subject into a search query.

The timing information may indicate timing requirements of the caretaking needs. Timing requirements may include one or more of start date, start time, end date, end time, and/or other information.

The location information may indicate location where the caretaking is to take place. The location information may include one or more of the value of the location parameter stored in the seeker profiles. By way of non-limiting illustration, individual user interface elements may correspond to individual locations included in a seeker profile. User input into the individual user interface elements (e.g., selection of a checkbox) may incorporate the information about the location into a search query.

A display portion may be configured to display responses from user-provided search queries (see, e.g., search component 112). The responses may include sets of one or more provider profiles having one or more characteristics that satisfy the user-defined search queries. By way of non-limiting illustration, a provider profile may be displayed based on having characteristics (defined in values of provider parameters) satisfying one or more of subject information, timing information, location information, and/or other information included in the user defined search queries. In some implementations, individual provider profiles in the sets of one or more provider profiles may be displayed in a list form and/or other display form. In some implementations, individual provider profiles may be associated with individual user interface elements (e.g., check boxes) configured to facilitate selection of an associated provider profile. The display portion may be configured to receive user entry and/or selection of one or more provider profiles from the displayed individual sets of one or more provider profiles. The entry and/or selection may convey a desire to utilize the particular care provider for caretaking needs. The entry and/or selection of one or more provider profiles may generate and communicate caretaking requests to computing platforms of the one or more care providers of the one or more provider profiles (see, e.g., request component 114).

In some implementations, a display portion as viewed on a user interface of a care provider may include one or more caretaking requests and/or other information. Individual caretaking requests may include one or more of subject information, timing information, location information, and/or other information included in the user defined search query. The display portion showing a caretaking request may include a user interface element configured to obtain entry and/or selection to accept, deny, and/or modify the caretaking request. The acceptance, denial, and/or modification may be communicated back to a computing platform of the requesting care seeker (see, e.g., booking component 115).

The profile component 108 may be configured to effectuate communication of notifications to the individual potential care providers. The notifications may be generated and/or communicated responsive to the user entry and/or selection by the individual care seekers of the individual sets of characteristics of the individual potential care providers. The notifications may convey to the individual potential care providers a pending request for them to become a care provider. In some implementations, the notifications may include further instructions on how to complete the process of becoming a care provider. The instructions may include one or more of confirming identity, inputting information into a profile, contacting a representative of the system, signing documents, passing a background check, and/or other information.

The profile component 108 may be configured to generate new individual provider profiles for the individual potential care providers. The new provider profiles may be generated responsive to obtaining indications that the individual potential care providers are approved. In some implementations, new provider profiles may be generated based on individual sets of characteristics of the individual potential care providers provided by the care seekers, information provided by the potential care providers themselves, and/or other information. In some implementations, representatives and/or administrators of system 100 may provide input indicating approval of potential care providers in response to completion of one or more of the instructions to become a care provider.

The generation of the new provider profile may cause the individual potential care providers to be defined as users who are individual care providers within the system 100. By way of non-limiting illustration, a second provider profile may be generated for the first potential care provider such that the first potential care provider may be deemed a third user of the system 100 who is an individual care provider.

The search component 112 may be configured to obtain, via user interface component 110, one or more user-provided search queries. Search component 112 may be configured to search stored provider profiles for one or more provider profiles having one or more characteristics matching individual ones of the user-provided search queries. A match may refer to one or more of an exact match, a logically similar match, and/or other consideration of determining search results. A logically similar match may refer to a match that may not be exact (e.g., have the exact same text or phrasing), but may include text or phrases represented by different words that otherwise mean the same thing. By way of non-limiting illustration, a logically similar match may be found between a query of "caretaking is required on Saturday" and a provider profile indicating "I work weekends." By way of non-limiting illustration, an exact match may be found between a query of "caretaking is required at a personal residence in San Diego" and a provider profile specifying "I am willing to travel throughout San Diego."

The search component 112 may be configured to identify individual sets of one or more provider profiles based on the user defined search queries. The individual sets of one or more provider profiles may include the individual provider profiles having one or more characteristics that satisfy one or more of subject information, timing information, location information and/or other information included in the user defined search queries. By way of non-limiting illustration, a first set of provider profiles may be identified based on a first user defined search query by the first user. The first set of provider profiles may include the first provider profile, the second provider profile, and/or other provider profiles satisfying the first user-defined search query. The search component 112 may be configured to communicate the identified individual sets of one or more provider profiles to the user interface component 110 for display on the computing platform of the first user.

The request component 114 may be configured to receive, via input into the user interface, user entry and/or selection of one or more provider profiles from the individual sets of one or more provider profiles displayed as a result of search by search component 112. By way of non-limiting illustration, an entry and/or selection of the second provider profile (and/or other provider profile) from the first set of provider profiles displayed on the user interface of the first computing platform of the first user may be received.

In some implementations, request component 114 may be configured to access and/or identify one or more provider profiles of care providers previously used to satisfy caretaking needs. In some implementations, a care seeker may save a list of one or more provider profiles so that individual profiles may be selected on later occasions. By way of non-limiting illustration, a care seeker may create a "favorites" list (e.g., within their seeker profile) of provider profiles of care providers. In some implementations, a saved list of provider profiles of care providers may be displayed on a user interface in a list form and/or other display form. In some implementations, individual provider profiles may be associated with individual user interface elements (e.g., check boxes) configured to facilitate selection of an associated provider profile. The request component 114 may be configured to receive, via input into the user interface, user entry and/or selection of one or more provider profiles from a saved list of provider profiles.

The request component 114 may be configured to generate individual caretaking requests. The individual caretaking requests may include one or more of subject information, timing information, location information, and/or other information included in the user defined search queries. In some implementations, individual caretaking requests may include the seeker profiles of the care seekers who are requesting the caretaking. This may allow the care providers to review the care seeker profiles before accepting the job. By way of non-limiting illustration, request component 114 may be configured to generate a first caretaking request based on information in the first user defined search query. The first caretaking request may include the first seeker profile of the first user and/or other information.

The request component 114 may be configured to effectuate communication of the individual caretaking requests to individual computing platforms associated with individual ones of the one or more provider profiles. The individual caretaking requests may include a user interface element configured to obtain entry and/or selection to accept, deny, and/or modify the caretaking request. The acceptance, denial, and/or modification may be communicated back to a computing platform of the requesting care seeker. By way of non-limiting illustration, request component 114 may be configured to effectuate communication of the first caretaking request to a computing platform of the third user.

The booking component 115 may be configured to obtain entry and/or selection by the individual care providers to accept, deny, and/or modify the caretaking requests. The selection of an "accept" may cause an acceptance notification to be sent back to the computing platform of the care seeker. The acceptance notification may include confirmation of subject information, timing information, location information, and/or other information. The selection of a "deny" may cause a denial notification to be sent back to the computing platform of the care seeker. The denial notification may include an indication that the request was not accepted, a reason why, and/or other information. The selection of a "modify" may cause a request modification notification to be sent back to the computing platform of the care seeker. The request modification notification may include proposed changes to subject information, timing information, location information, and/or other information.

The booking component 115 may be configured to obtaining indications that the caretaking has been completed. By way of non-limiting illustration, one or both of individual care seekers and/or individual care providers may provide input into a user interface indication completion of a caretaking request. Responsive to obtaining indications that the caretaking has been completed, booking component 115 may be configured to effectuate communication of payment information to the individual computing platforms of the individual care providers. The payment information may include information necessary to effectuate funds being deducted from a funds source of a care seeker (e.g., based on values of payment parameter in a seeker profile) and attributed to a funds source of a care provider (e.g., based on values of payment parameter in a provider profile).

The booking component 115 may be configured to determine payment amounts to be deducted from different funds sources of individual care seekers. By way of non-limiting illustration, costs subsidized by healthcare systems and/or employer benefits may be accompanied by an out-of-pocket co-pay. The booking component 115 may be configured to determine an amount of healthcare and/or employer paid costs and/or an amount of out-of-pocket co-pay costs.

Figures 3, 4:
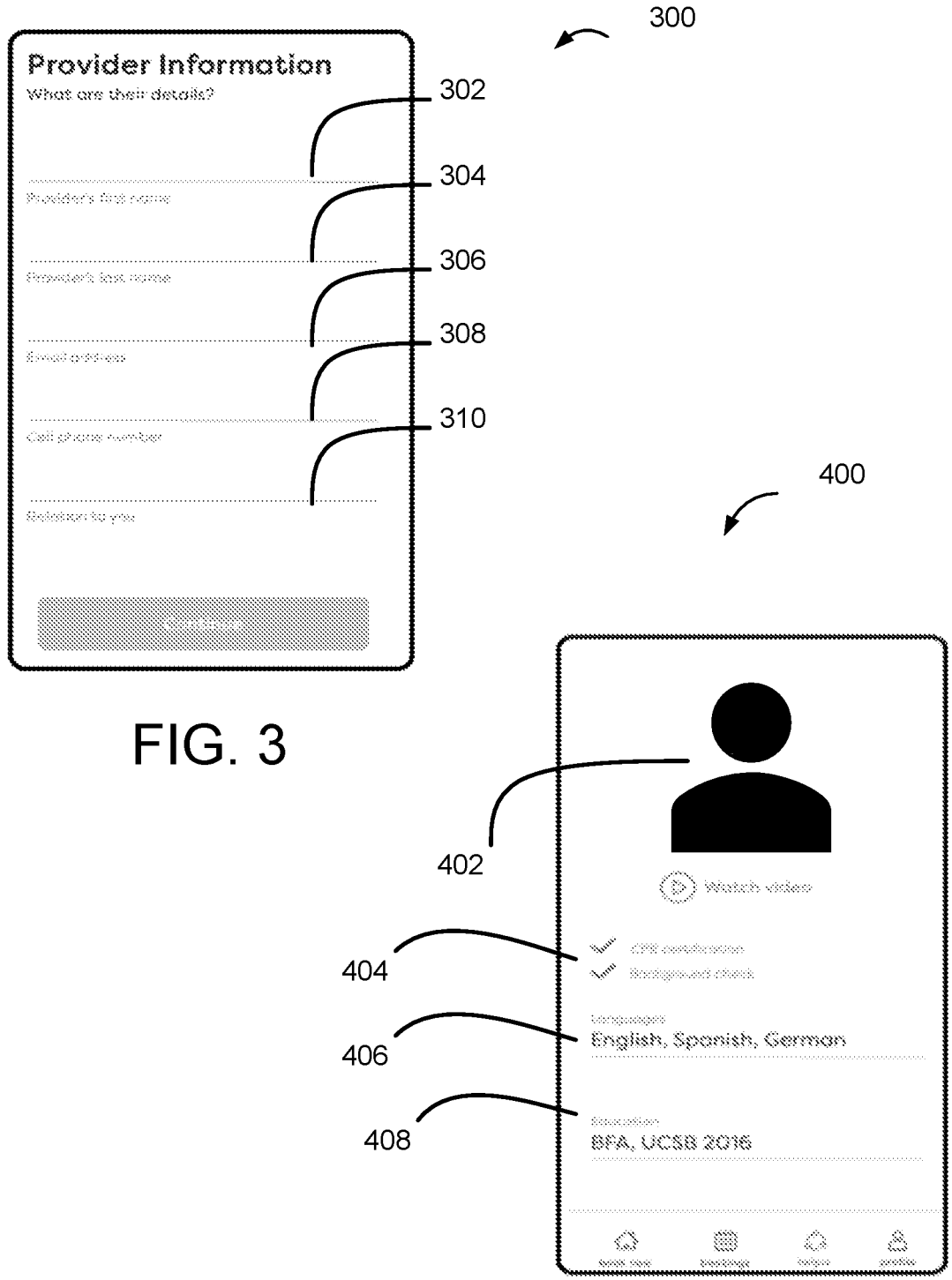
FIG. 3 illustrates an exemplary user interface, in accordance with one or more implementations.
FIG. 4 illustrates an exemplary user interface, in accordance with one or more implementations.

FIG. 3 illustrates an exemplary user interface 300, in accordance with one or more implementations. The user interface 300 may be configured to obtain user entry and/or selection of a set of characteristics of a potential care provider to facilitate generation of a provider profile for the potential care provider. The user interface 300 may include a set of user interface elements. Individual user interface elements may correspond to individual provider parameters. Individual user interface elements may include, for example, text input fields. By way of non-limiting illustration, a first element 302, a second element 304, a third element 306, and/or a fourth element 308 may correspond to different values of a name parameter. By way of non-limiting illustration, a fifth element 310 may correspond to a value of a relationship parameter.

FIG. 4 illustrates an exemplary user interface 400, in accordance with one or more implementations. The user interface 400 may be configured to display a provider profile. The user interface 400 may include a set of user interface elements. Individual user interface elements may correspond to display portions displaying different values of different provider parameters of a care provider and/or other information included in a provider profile. By way of non-limiting illustration, a first element 402 may display an image of the care provider, a second element 404 may display one or more values of a certification parameter, a third element 406 may display a value of a languages parameter, and/or a fourth element 408 may display values of an education parameter.

Figures 5, 6:
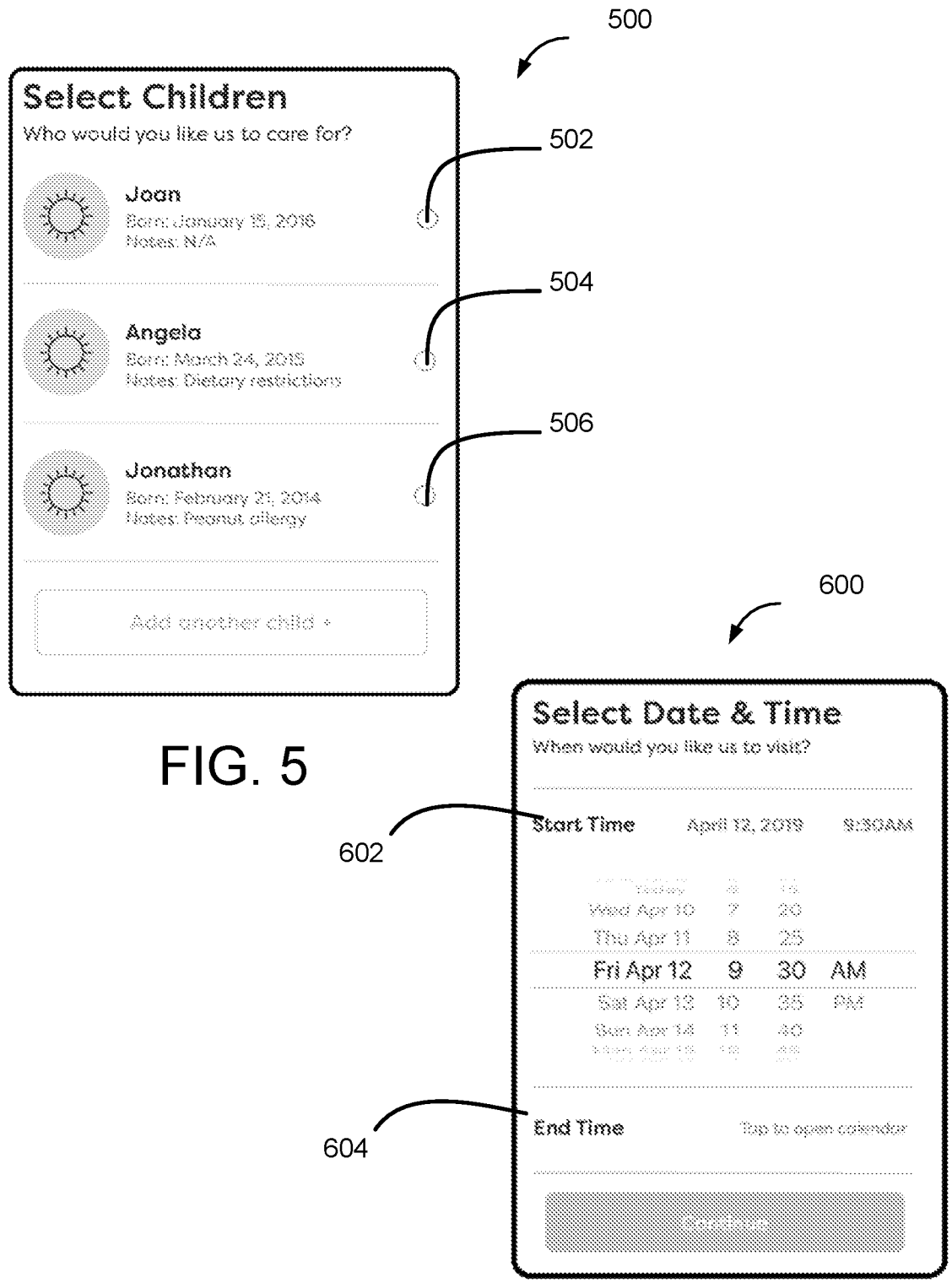
FIG. 5 illustrates an exemplary user interface, in accordance with one or more implementations.
FIG. 6 illustrates an exemplary user interface, in accordance with one or more implementations.

FIG. 5 illustrates an exemplary user interface 500, in accordance with one or more implementations. The user interface 500 may be configured to obtain user entry and/or selection of subject information to be included in a user defined search query. The user interface 500 may include a set of user interface elements. Individual user interface elements be selected and/or may correspond to individual subjects that may be included in a seeker profile. Individual user interface elements may include, for example, check boxes. By way of non-limiting illustration, a first element 502 may facilitate selection of a first subject, a second element 504 may facilitate selection of a second subject, and/or a third element 506 may facilitate selection of a third subject.

FIG. 6 illustrates an exemplary user interface 600, in accordance with one or more implementations. The user interface 600 may be configured to obtain user entry and/or selection of timing information to be included in a user defined search query. The user interface 600 may include a set of user interface elements. Individual user interface elements be selected and/or may correspond to timing requirements with respect to start date and/or time and/or end date and/or time. Individual user interface elements may include, for example, a scrolling date/time indicator. By way of non-limiting illustration, a first element 602 may facilitate selection of a start date and/or time, and/or a second element 604 may facilitate selection of an end date and/or time.

FIG. 7 illustrates an exemplary user interface 700, in accordance with one or more implementations. The user interface 700 may be configured to obtain user entry and/or selection of location information to be included in a user defined search query. The user interface 700 may include a set of user interface elements. Individual user interface elements be selected and/or may correspond to individual locations that may be included in a seeker profile. Individual user interface elements may include, for example, check boxes. By way of non-limiting illustration, a first element 702 may facilitate selection of a first location, a second element 704 may facilitate selection of a second location, and/or a third element 706 may facilitate selection of a third location.

FIG. 8 illustrates an exemplary user interface 800, in accordance with one or more implementations. The user interface 800 may be configured to display individual sets of one or more provider profiles satisfying a search query, and/or obtain user entry and/or selection of one or more provider profiles from the individual sets of one or more provider profiles. The user interface 800 may include a set of user interface elements. Individual user interface elements may be selected and/or may correspond to individual providers. Individual user interface elements may include, for example, check boxes. By way of non-limiting illustration, a first element 802 may facilitate selection of a first provider profile, a second element 804 may facilitate selection of a second provider profile, and/or a third element 806 may facilitate selection of a third provider profile.

FIG. 9 illustrates an exemplary user interface 900, in accordance with one or more implementations. The user interface 900 may include a display portion showing one or more of current bookings, pending bookings, past bookings, canceled bookings, and/or other information. The user interface 900 may serve as a hub to select individual bookings to cancel and/or modify individual bookings Returning to FIG. 1, in some implementations, server(s) 102, client computing platform(s) 104, and/or external resources 126 may be operatively linked via one or more electronic communication links. For example, such electronic communication links may be established, at least in part, via a network 116 such as the Internet and/or other networks. It will be appreciated that this is not intended to be limiting, and that the scope of this disclosure includes implementations in which server(s) 102, client computing platform(s) 104, and/or external resources 126 may be operatively linked via some other communication media.

A given client computing platform 104 may include one or more processors configured to execute computer program components. The computer program components may be configured to enable an expert or user associated with the given client computing platform 104 to interface with system 100 and/or external resources 126, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 126 may include sources of information outside of system 100, external entities participating with system 100, and/or other resources. In some implementations, some or all of the functionality attributed herein to external resources 126 may be provided by resources included in system 100. By way of non-limiting illustration, an external entity may include one or more of a bank, a healthcare provider, an employer, and/or other entities.

Server(s) 102 may include electronic storage 128, one or more processors 130, and/or other components. Server(s) 102 may include communication lines, or ports to enable the exchange of information with a network 116 and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 128 may comprise non-transitory storage media that electronically stores information. The electronic storage media of electronic storage 128 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 102, information received from client computing platform(s) 104, and/or other information that enables server(s) 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 108, 110, 112, 114, 115, and/or other components. Processor(s) 130 may be configured to execute components 108, 110, 112, 114, 115, and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, and/or 115 are illustrated in FIG. 1 as being implemented within a single processing unit, in implementations in which processor(s) 130 includes multiple processing units, one or more of components 108, 110, 112, 114, and/or 115 may be implemented remotely from the other components. The description of the functionality provided by the different components 108, 110, 112, 114, and/or 115 described below is for illustrative purposes, and is not intended to be limiting, as any of components 108, 110, 112, 114, and/or 115 may provide more or less functionality than is described. For example, one or more of components 108, 110, 112, 114, and/or 115 may be eliminated, and some or all of its functionality may be provided by other ones of components 108, 110, 112, 114, and/or 115. As another example, processor(s) 130 may be configured to execute one or more additional components that may perform some or all of the functionality attributed below to one of components 108, 110, 112, 114, and/or 115.

Figure 2:
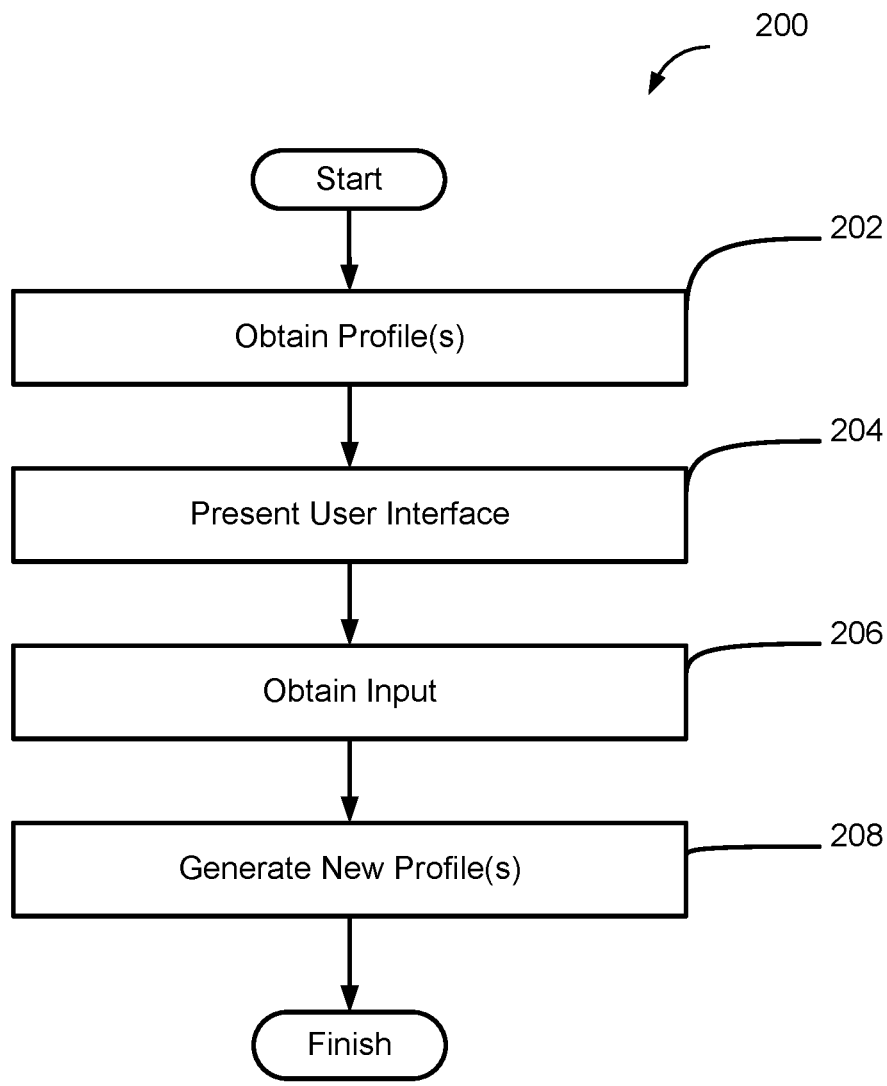
FIG. 2 illustrates a method to connect care seekers with care providers for caretaking needs, in accordance with one or more implementation

FIG. 2 illustrates a method 200 to connect care seekers with care providers for caretaking needs, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining one or more of seeker profiles for care seekers, provider profiles for care providers, and/or other information. Individual seeker profiles may define values of seeker parameters. The values of the seeker parameters may describe characteristics of the care seekers. The seeker profiles may comprise a first seeker profile for a first user who is an individual care seeker. Individual provider profiles may define values of provider parameters. The values of the provider parameters may describe characteristics of the care providers. The provider profiles may comprise a first provider profile for a second user who is an individual care provider. Operation 202 may be performed by one or more hardware processors configured by machine-readable instructions including a component that is the same as or similar to profile component 108, in accordance with one or more implementations.

An operation 204 may include presenting a user interface on computing platforms of users. The user interface may be configured to facilitate generation of the individual provider profiles by individual care seekers. By way of non-limiting illustration, the user interface may be presented on a first computing platform of the first user. Operation 204 may be performed by one or more hardware processors configured by machine-readable instructions including a component that is the same as or similar to user interface component 110, in accordance with one or more implementations.

An operation 206 may include receiving, via the user interface, user entry and/or selection by the individual care seekers of individual sets of characteristics of individual potential care providers. By way of non-limiting illustration, user entry and/or selection of a first set of characteristics of a first potential care provider may be received from the first user via the user interface. Operation 206 may be performed by one or more hardware processors configured by machine-readable instructions including a component that is the same as or similar to user interface component 110 and/or profile component 108, in accordance with one or more implementations.

An operation 208 may include generating new individual provider profiles for individual potential care providers. The individual potential care providers may subsequently be defined as users who are individual care providers. By way of non-limiting illustration, a second provider profile may be generated for the first potential care provider such that the first potential care provider may comprise a third user who is an individual care provider. Operation 208 may be performed by one or more hardware processors configured by machine-readable instructions including a component that is the same as or similar to profile component 108, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to connect care seekers with care providers for caretaking needs, the system comprising:
    non-transitory electronic storage storing:
        seeker profiles for users who are defined as care seekers, individual ones of the seeker profiles defining values of seeker parameters, the values of the seeker parameters describing characteristics of individual ones of the care seekers, the seeker profiles comprising a first seeker profile for a first user who is one of the care seekers; and
        provider profiles for the users who are defined as care providers, individual ones of the provider profiles defining values of provider parameters, the values of the provider parameters describing characteristics of individual ones of the care providers, the provider profiles comprising a first provider profile for a second user who is one of the care providers; and
    one or more physical processors configured by machine-readable instructions to:
        effectuate presentation of a user interface on computing platforms associated with the users who are the care seekers, the user interface being configured to facilitate generation of new ones of the provider profiles by the individual ones of the care seekers so that the new ones of the provider profiles are for new users who i) are defined by the individual ones of the care seekers themselves, and ii) become new ones of the care providers, such that the user interface is presented on a first computing platform associated with the first user who is one of the care seekers;
        receive, via the user interface, user entry and/or selection of individual sets of characteristics of the new users as defined by the individual ones of the care seekers, an individual characteristic including a relationship characteristic comprising an indication of a relationship between the individual ones of the care seekers and the new users, the relationship including one or more of grandparent, sister, brother, in-law, friend, friend-of-friend, or neighbor, such that first user entry and/or selection of a first set of characteristics of a first new user is received from the first user via the user interface; and
        generate, based on the individual sets of characteristics of the new users, the new ones of the provider profiles for the new users so that the new users are thereafter defined as the care providers and are available for selection by the care seekers to fulfill care-seeking needs of the care seekers, such that a second provider profile is generated for the first new user so that the first new user is one of the care providers and is available to be selected by the first user and one or more other ones of the care seekers to fulfill care-seeking needs.

2. The system of claim 1, wherein the one or more physical processors are further configured by the machine-readable instructions to:
    responsive to the user entry and/or selection of the individual sets of characteristics of the new users, effectuate communication of notifications to the new users; and
    responsive to obtaining indications that the new users are approved, generate the new ones of the provider profiles.

3. The system of claim 1, wherein the one or more physical processors are further configured by the machine-readable instructions to:
    effectuate presentation of a second user interface on the computing platforms associated with the new users, the second user interface being configured to obtain further user entry and/or selection of further characteristics of the new users; and
    responsive to obtaining the further user entry and/or selection of the further characteristics of the new users, generate the new ones of the provider profiles.

4. The system of claim 1, wherein the one or more physical processors are further configured by the machine-readable instructions to:
    receive, via the user interface, user defined search queries, an individual user defined search query indicating subject information, timing information, and location information, the subject information identifying and/or describing one or more subjects having caretaking needs, the timing information indicating timing requirements of the caretaking needs, and the location information indicating location where the caretaking is to take place;
    identify individual sets of one or more of the provider profiles based on the user defined search queries, the individual sets of one or more of the provider profiles including the provider profiles having one or more of the characteristics that satisfy one or more of the subject information, the timing information, or the location information, such that a first set of the provider profiles is identified based on a first user defined search query submitted by the first user, the first set of the provider profiles including the first provider profile and the second provider profile;
    display, via the user interface, the individual sets of one or more of the provider profiles, including displaying the first set of the provider profiles on the user interface displayed on the first computing platform associated with the first user;
    receive, via the user interface, subsequent user entry and/or selection of one or more of the provider profiles from the individual sets of one or more of the provider profiles, including receiving a second entry and/or selection of the second provider profile from the first set of the provider profiles displayed on the user interface of the first computing platform associated with the first user;
    generate individual caretaking requests, the individual caretaking requests including one or more of the subject information, the timing information, or the location information included in the user defined search queries, including generating a first caretaking request based on information in the first user defined search query; and
    effectuate communication of the individual caretaking requests to individual ones of the computing platforms associated with the users who are the care providers, such that the first caretaking request is communicated to a second computing platform associated with the first new user.

5. The system of claim 4, wherein the one or more physical processors are further configured by the machine-readable instructions to:
    responsive to obtaining indications that the caretaking needs have been completed, effectuate communication of payment information to the individual ones of the computing platforms associated with the users who are the care providers.

6. The system of claim 1, the characteristics of the individual ones of the care providers include one or more of name, location, age, experience, fluent languages, certifications, education, cost, caretaking specialties, or relationship to user.

7. The system of claim 1, wherein the one or more physical processors are further configured by the machine-readable instructions to:

generate new ones of the seeker profiles based other new users submitting requests to become the care seekers.

8. The system of claim 1, wherein the one or more physical processors are further configured by the machine-readable instructions to:

obtain, via the user interface, further user entry and/or selection by the new users to generate the new ones of the provider profiles.

9. The system of claim 1, wherein the individual ones of the seeker profiles for the individual ones of the care seekers further include individual lists of one or more of the provider profiles of the care providers previously used.

10. A non-transitory electronic storage media, the non-transitory electronic storage media storing instruction which, when executed by a computer system, cause the computer system to perform a method of:

obtaining seeker profiles for users who are defined as care seekers, individual ones of the seeker profiles defining values of seeker parameters, the values of the seeker parameters describing characteristics of individual ones of the care seekers, the seeker profiles comprising a first seeker profile for a first user who is one of the care seekers;

obtaining provider profiles for the users who are defined as care providers, individual ones of the provider profiles defining values of provider parameters, the values of the provider parameters describing characteristics of individual ones of the care providers, the provider profiles comprising a first provider profile for a second user who is one of the care providers;

effectuating presentation of a user interface on computing platforms associated with the users who are the care seekers, the user interface being configured to facilitate generation of new ones of the provider profiles by the individual ones of the care seekers so that the new ones of the provider profiles are for new users who i) are defined by the individual ones of the care seekers themselves, and ii) become new ones of the care providers, including effectuating presentation of the user interface on a first computing platform associated with the first user who is one of the care seekers;

receiving, via the user interface, user entry and/or selection of individual sets of characteristics of the new users as defined by the individual ones of the care seekers, an individual characteristic including a relationship characteristic comprising an indication of a relationship between the individual ones of the care seekers and the new users, the relationship including one or more of grandparent, sister, brother, in-law, friend, friend-of-friend, or neighbor, including receiving first user entry and/or selection of a first set of characteristics of a first new user from the first user via the user interface; and generating, based on the individual sets of characteristics of the new users, the new ones of the provider profiles for the new users so that the new users are thereafter defined as the care providers and are available for selection by the care seekers to fulfill care-seeking needs of the care seekers, including generating a second provider profile for the first new user so that the first new user is one of the care providers and is available to be selected by the first user and one or more other ones of the care seekers to fulfill care-seeking needs.

11. The non-transitory electronic storage media of claim 10, wherein the method further comprises:

responsive to the receiving of the user entry and/or selection, effectuating communication of notifications to the new users; and responsive to obtaining indications that the new users are approved, generating the new ones of the provider profiles.

12. A method to connect care seekers with care providers for caretaking needs, the method comprising:

obtaining seeker profiles for users who are defined as care seekers, and provider profiles for the users who are defined as care providers, individual ones of the seeker profiles defining values of seeker parameters, the values of the seeker parameters describing characteristics of individual ones of the care seekers, the seeker profiles comprising a first seeker profile for a first user who is one of the care seekers, individual ones of the provider profiles defining values of provider parameters, the values of the provider parameters describing characteristics of individual ones of the care providers, the provider profiles comprising a first provider profile for a second user who is one of the care providers;

effectuating presentation of a user interface on computing platforms associated with the users who are the care seekers, the user interface being configured to facilitate generation of new ones of the provider profiles by the individual ones of the care seekers so that the new ones of the provider profiles are for new users who i) are defined by the individual ones of the care seekers themselves, and ii) become new ones of the care providers, including effectuating presentation of the user interface on a first computing platform associated with the first user who is one of the care seekers;

receiving, via the user interface, user entry and/or selection of individual sets of characteristics of the new users as defined by the individual ones of the care seekers, an individual characteristic including a relationship characteristic comprising an indication of a relationship between the individual ones of the care seekers and the new users, the relationship including one or more of grandparent, sister, brother, in-law, friend, friend-of-friend, or neighbor, including receiving first user entry and/or selection of a first set of characteristics of a first new user from the first user via the user interface; and generating, based on the individual sets of characteristics of the new users, the new ones of the provider profiles for the new users so that the new users are thereafter defined as the care providers and are available for selection by the care seekers to fulfill care-seeking needs of the care seekers, including generating a second provider profile for the first new user so that the first new user is one of the care providers and is available to be selected by the first user and one or more other ones of the care seekers to fulfill care-seeking needs.

13. The method of claim 12, further comprising:

responsive to the user entry and/or selection of the individual sets of characteristics of the new users, effectuating communication of notifications to the new users; and responsive to obtaining indications that the new users are approved, generating the new ones of the provider profiles.

14. The method of claim 12, further comprising:

effectuating presentation of a second user interface on the computing platforms of the new users, the second user interface being configured to obtain further user entry and/or selection of further characteristics of the new users; and responsive to obtaining the further user entry and/or selection of the further characteristics of the new users, generating the new ones of the provider profiles.

15. The method of claim 12, further comprising:

receiving, via the user interface, user defined search queries, an individual user defined search query indicating subject information, timing information, and location information, the subject information identifying and/or describing one or more subjects having caretaking needs, the timing information indicating timing requirements of the caretaking needs, and the location information indicating location where the caretaking is to take place;

identifying individual sets of one or more of the provider profiles based on the user defined search queries, the individual sets of one or more of the provider profiles including the provider profiles having one or more of the characteristics that satisfy one or more of the subject information, the timing information, or the location information, including identifying a first set of the provider profiles based on a first user defined search query submitted by the first user, the first set of the provider profiles including the first provider profile and the second provider profile;

displaying, via the user interface, the individual sets of one or more of the provider profiles, including displaying the first set of the provider profiles on the user interface displayed on the first computing platform associated with the first user;

receiving, via the user interface, subsequent user entry and/or selection of one or more of the provider profiles from the individual sets of one or more of the provider profiles, including receiving a second entry and/or selection of the second provider profile from the first set of the provider profiles displayed on the user interface of the first computing platform associated with the first user;

generating individual caretaking requests, the individual caretaking requests including one or more of the subject information, the timing information, or the location information included in the user defined search queries, including generating a first caretaking request based on information in the first user defined search query; and effectuating communication of the individual caretaking requests to individual ones of the computing platforms associated with the users who are the care providers, including effectuating communication of the first caretaking request to a second computing platform associated with the first new user.

16. The method of claim 15, further comprising:

responsive to obtaining indications that the caretaking needs have been completed, effectuating communication of payment information to the individual ones of the computing platforms associated with the users who are the care providers.

17. The method of claim 12, wherein the characteristics of the individual ones of the care providers include one or more of name, location, age, experience, fluent languages, certifications, education, cost, caretaking specialties, or relationship to user.

18. The method of claim 12, further comprising:

generating new ones of the seeker profiles based other new users submitting requests to become the care seekers.

19. The method of claim 12, further comprising:

obtaining, via the user interface, further user entry and/or selection by the new users to generate the new ones of the provider profiles.

20. The method of claim 12, wherein the individual ones of the seeker profiles for the individual ones of the care seekers further include individual lists of one or more of the provider profiles of the care providers previously used.

* * * * *